United States Patent
Billings

[11] Patent Number: 5,484,124
[45] Date of Patent: Jan. 16, 1996

[54] NON-TACTUAL FACILITATION SUPPORT SYSTEM

[76] Inventor: Donald Billings, 8 Sycamore Pl., East Northport, Long Island, N.Y. 11731

[21] Appl. No.: 25,559

[22] Filed: Mar. 3, 1993

[51] Int. Cl.⁶ .................................................. B68G 5/00
[52] U.S. Cl. ...................... 248/118; 248/454; 248/918; 400/489; 434/112
[58] Field of Search .................. 248/118, 118.1, 248/447, 454, 455, 918, 441.1, 542; 341/21; 340/825.19; 400/489, 492; 434/112–117; 345/156, 168, 173; 116/306, 325, 328, 332, 236, 238, 239; 606/1; 273/148 B, 438

[56] References Cited

U.S. PATENT DOCUMENTS

| | | | |
|---|---|---|---|
| 1,652,774 | 12/1927 | Fraser et al. | 248/542 X |
| 1,767,950 | 6/1930 | Westbrook | 248/454 |
| 4,069,995 | 1/1978 | Miller | 248/118.1 |
| 4,913,390 | 4/1990 | Berke | 248/918 X |
| 5,076,079 | 12/1991 | Monoson et al. | 248/680 |
| 5,219,136 | 6/1993 | Hassel et al. | 248/118 |
| 5,281,001 | 1/1994 | Bergsten et al. | 248/118 X |

Primary Examiner—Blair M. Johnson
Attorney, Agent, or Firm—Morgan & Finnegan

[57] ABSTRACT

An apparatus for facilitating a person's use of a communication device consisting of an easel for supporting a communication device and an appendage support. The easel and the appendage support cooperate with a person's appendage to facilitate use of a communication device.

11 Claims, 6 Drawing Sheets

FIG. 3A
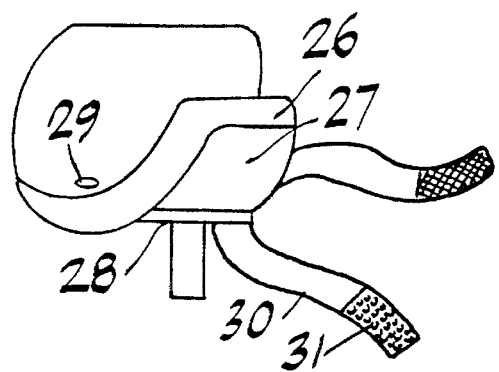
FIG. 3B
FIG. 3C
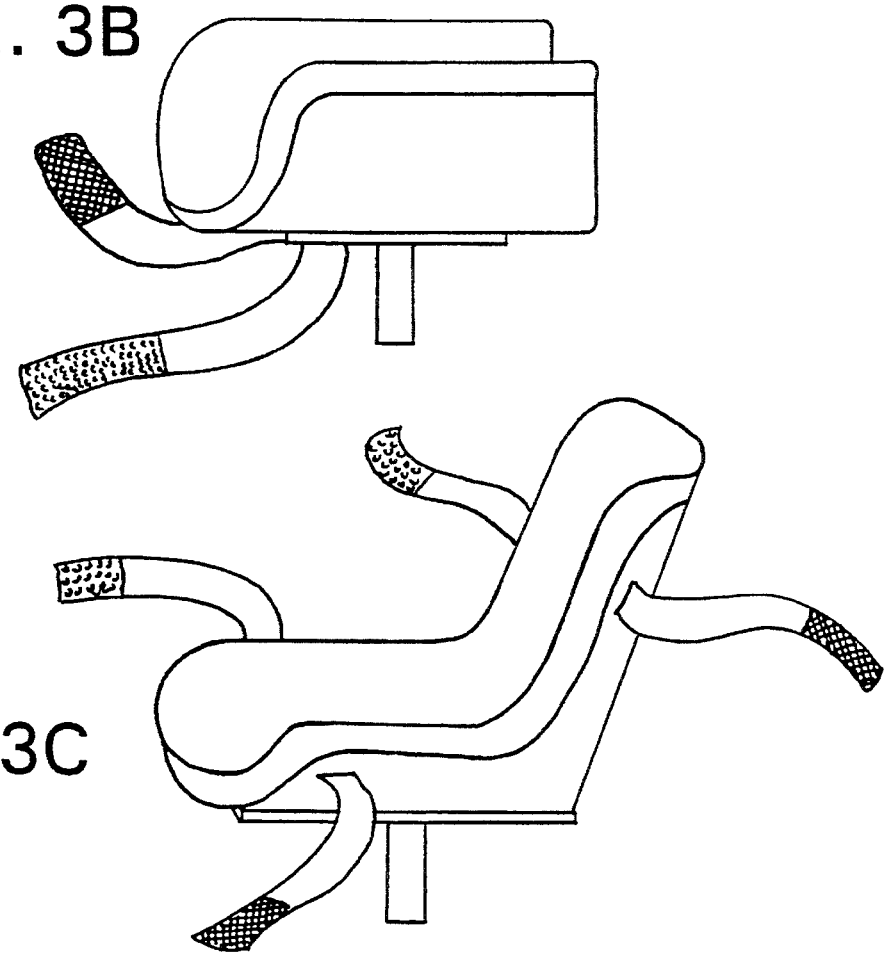

NON-TACTUAL FACILITATION SUPPORT SYSTEM

BACKGROUND OF THE INVENTION

The present invention pertains to an apparatus for facilitating and aiding a person's use of a communication device. In particular, the present invention pertains to a facilitation system having an easel for supporting a communication device and a human appendage cradle for cradling a person's hand or other appendage. The easel and the human appendage cradle cooperate with the person to facilitate use of the communication device, thus making unnecessary the use of a human facilitator.

A person with a communication disability or impairment may require a non-verbal communication method to convey his or her thoughts. Examples of non-verbal communication methods are written language, sign language, and use of a communication device. Many different types of communication devices may be used in the system of the present invention. A communication device, for instance, may be a typewriter or a computer keyboard. The device may also be a communication board which may have pictures which represent the needs of a person, e.g., a cup of juice, a favorite toy, a toilet, etc. A person points to a picture to convey to another person what he or she wants or needs. A communication board which displays the alphabet may be used to spell words by pointing to letters in succession.

Many people with communication disability or impairment can communicate using written language or sign language. Some autistic students have also been taught sign language. However, these methods require neuromotor skills which are often lacking. As a result, many disabled people are unable to express their thoughts on a full range of subjects using these methods. For these people, communication is limited.

Clinicians and researchers have found that some language impaired people can use a keyboard to point to or to type clearly articulated and relatively substantial statements and feelings through a technique called facilitated communication. Facilitated communication was developed in the 1970's in Australia by Rosemary Crossley. Significant work in the field of facilitated communication has also been done by Douglas Biklen of Syracuse University. See 60 Harvard Educational Review 3 (1990).

Facilitated communication "involves a facilitator who provides physical support to help stabilize the arm, to isolate the index finger if necessary to pull back the arm after each selection, to remind the individual to maintain focus; and to offer emotional support and encouragement . . . " Biklen et al., Facilitated Communication: Implications for individuals with autism, 12 Topics in Language Disorders 1–28 (1992). Currently, facilitated communication requires a trained facilitator who, during communication, supports the person's hand, arm, or elbow while the person types out a message. The facilitator is generally someone with whom the language impaired person has developed trust and rapport.

Crossley found that severe communication impairment is sometimes compounded by other neuromotor problems. Various neuromotor problems which impact a disabled person's ability to use written language have been identified: hand tremors; radial/ulnar muscle instability; muscle tone problems; poor eye-hand coordination; and other motor problems, as well as sensory processing disabilities.

Crossley's work indicates that the degree of facilitator contact with the language disabled student varies from individual to individual. Sometimes, the hand or wrist is supported. Other times, a hand held above the arm or on the shoulder is sufficient to enable the person to communicate.

Some recent research has concluded that human facilitators have unconsciously influenced the keyboard communication, and that the communication is not considered valid. Proponents of facilitated communication point to design flaws in these studies. Some of these studies use separate earphones to direct questions to the facilitator which are different than the questions to the subjects in the study. Other studies show pictures to the facilitator which are different than the pictures shown to the subject while separating the facilitator and the subject with a screen. The results lead some to the conclusion that the facilitator influences the language typed out during facilitated communication.

Many language disabled lack the motor skills to use the communication devices independently. They require physical support for their hand or arm and varying degrees of resistance. Facilitated communication offers this physical support. However, the resulting communication may be influenced by the facilitator. Thus there is a need for a system of communication which may be operated independently and which is not subject to the influence of a human facilitator. There is a need for a system of assisted communication which can adapt to the amount and type of support required by the individual.

SUMMARY OF THE INVENTION

Therefore, one of the objects of the invention is to provide a method and apparatus for assisted communication that cannot be consciously or unconsciously influenced by a human facilitator. Another object of the invention is to provide a method and apparatus for assisted communication that is responsive to the amount and type of support required by an individual using the system. The invention may be useful for teaching and assisting a person with impaired motor skills (e.g. a person with cerebral palsy) to use a computer or typewriter by holding and keeping the person's hand steady.

In accordance with these objectives, the invention is used as an aid to steady or stabilize a person's appendage, such as a person's hand, wrist, arm, or elbow while the person is using a communication device or keyboard communicator to communicate information.

To this end, the present invention provides an apparatus for facilitating or aiding a person's use of a communication device or keyboard communicator. The invention comprises an easel for supporting the communication device, and a human appendage support for positioning the person's appendage, such as the person's hand, wrist, arm or elbow. The human appendage support is operatively associated with the easel. The easel and the human appendage support cooperate with each other and with the person's appendage to facilitate use of the communication device. The invention may include a base on which the easel is mounted. The human appendage support (hereinafter referred to as the "appendage support") may also be mounted onto the base. The invention may also include a return prompt tether for providing added resistance against movement of the appendage support and a facilitator control handle for guiding a person's appendage while the person's appendage is supported by or is holding onto the appendage support.

In addition, the invention may be used to provide resistance to a person's hand, wrist, arm, or elbow during use of a communication device or keyboard communicator. The invention is especially useful with a tactually defensive person (an individual who does not want to be touched by others).

The present invention allows for close psychological support from a person such as a parent, therapist or teacher in an environment of reduced stimuli to produce communication that cannot be influenced even unconsciously by the facilitator. In addition, this invention will be useful to researchers attempting to settle the dispute over the degree of facilitator influence in facilitated communication.

BRIEF DESCRIPTION OF THE DRAWINGS

The structure, operation and advantages of this invention will become further apparent upon consideration of the following description in conjunction with the accompanying drawings, wherein:

FIG. 3 is a plain view of three types of supports:

3a. Hand cradle-type support;

3b. Arm-rest-type support; and

3c. Elbow cradle-type support

Figure 4A:
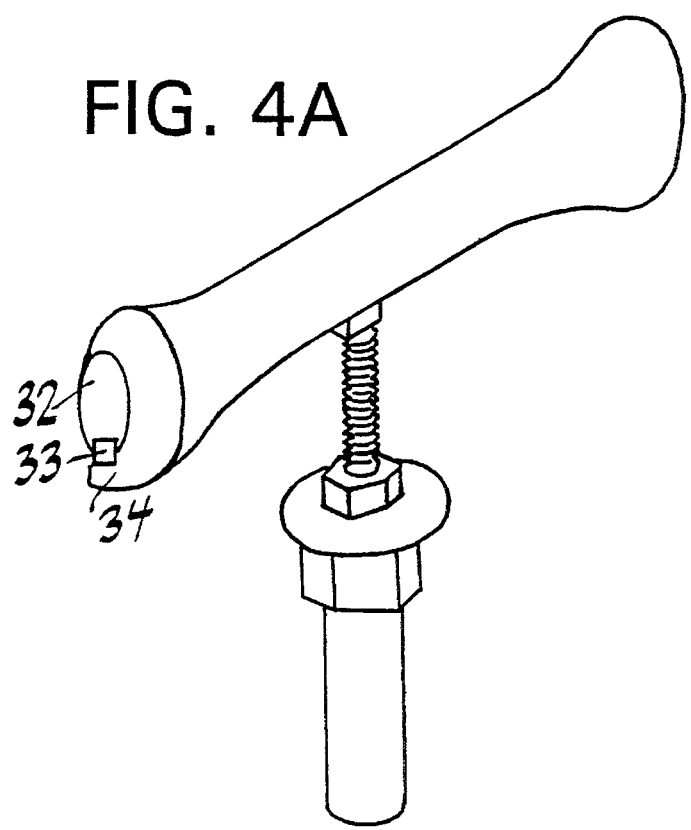

FIG. 4A is a perspective view of a t-bar-type support showing the mount which holds it to the forward resistance spring.

Figure 4B:
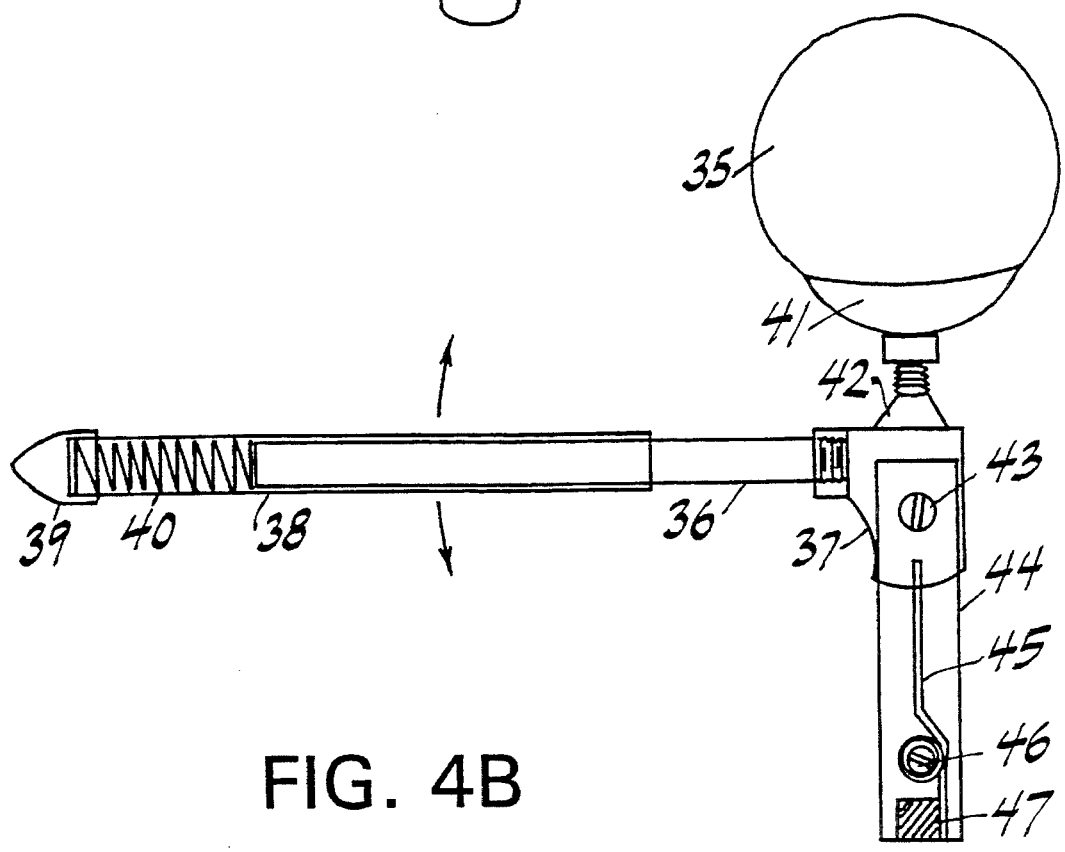

FIG. 4B is a plain view showing internal parts of a pointer-grip-type support.

Figure 4C:
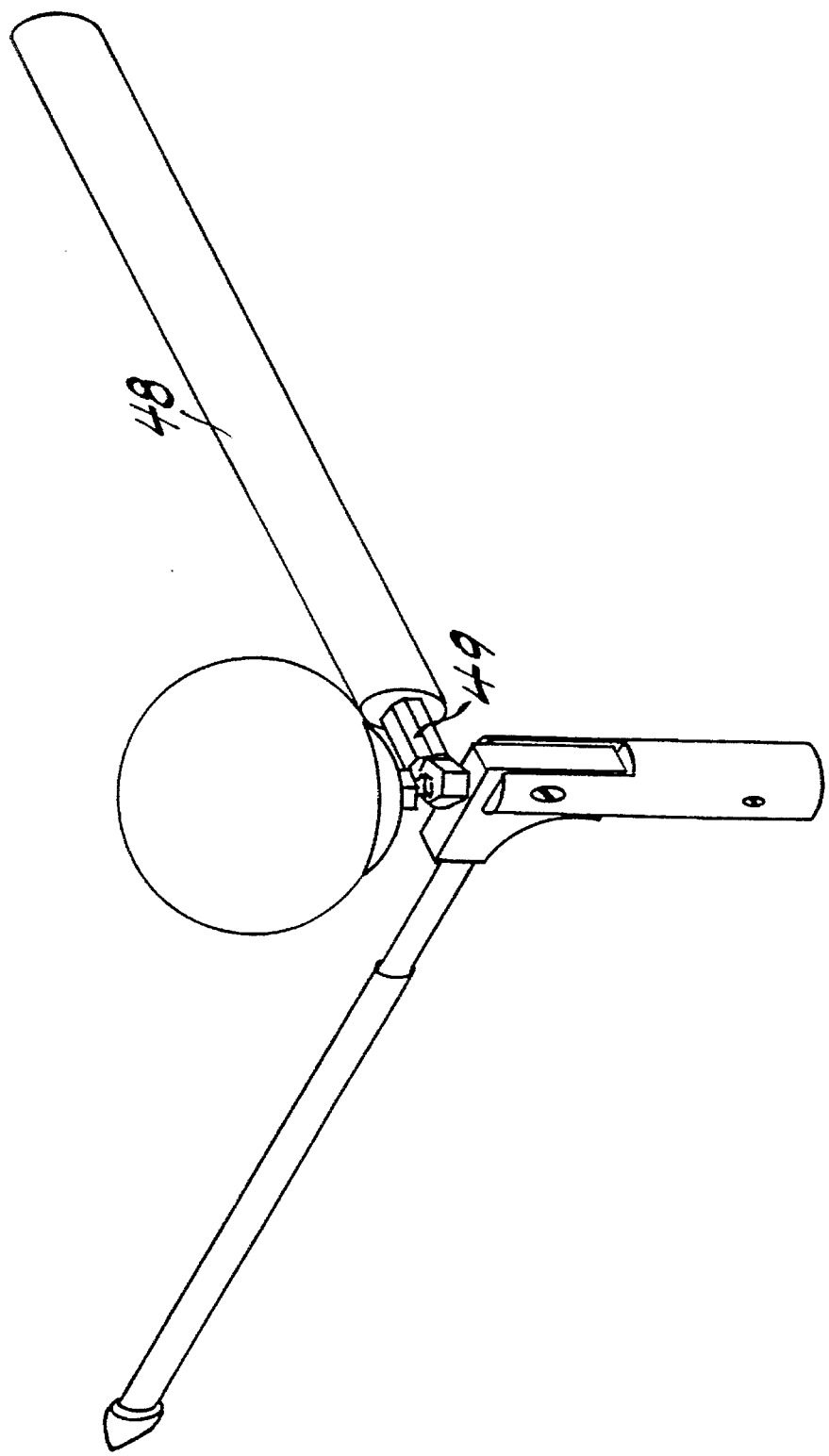

FIG. 4C is a perspective view of a pointer-grip-type support showing the facilitator control handle attached.

Figure 5:
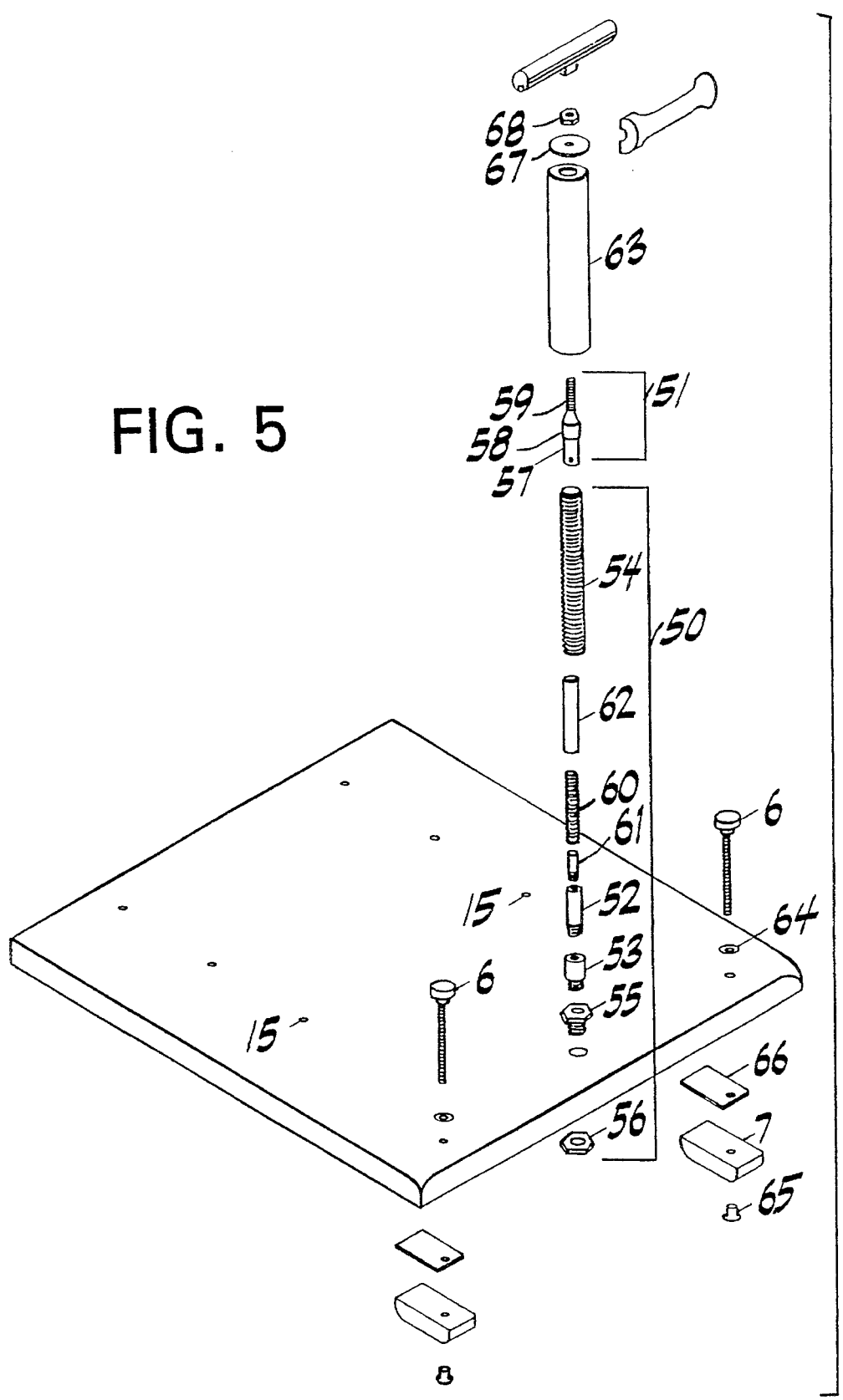

FIG. 5 is an exploded view with separated parts of the t-bar-type support, a forward resistance spring assembly, a spring assembly support mount and the base with desk-top clamps and easel mount holes.

DETAILED DESCRIPTION OF THE PREFERRED EMBODIMENTS

Figure 1:
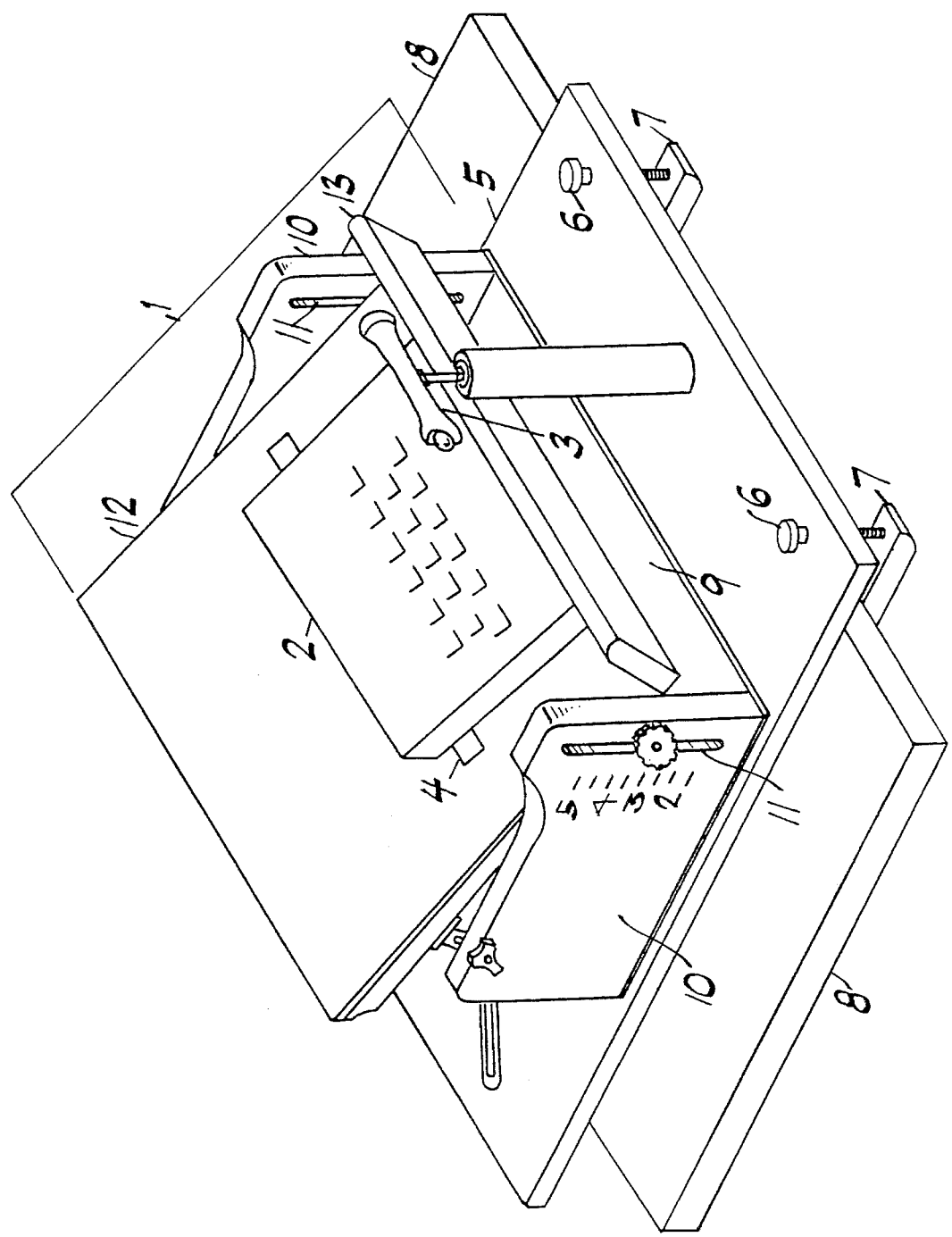
FIG. 1 is a front perspective view of an embodiment of the invention with a t-bar-type support.

Referring to FIG. 1, the invention comprises an easel 1, for supporting the communication device 2, and an appendage support 3 for holding a person's appendage, such as a person's hand, wrist, arm or elbow. The appendage support 3 is operatively associated with the easel 1. The easel 1 and the appendage support 3 cooperate with each other and with the person's appendage to facilitate use of the communication device 2.

The invention may be used with many types of communication devices 2. For example, the communication device 2 may be a communication board which may have pictures or display an alphabet. For autistic and other language disabled people, the communication device 2 may be a keyboard communicator such as an electric typewriter, a computer, or a communication device such as the Cannon CC7P Communicator or the Epson HX20 which have built-in printers.

The invention includes an easel 1 for supporting the communication device 2. In one embodiment, the easel 1 is made of heavy duty material to hold a standard electric typewriter. The easel 1 may be reinforced at stress points and may include a modified angle adjustment bar which uses steel angle iron for the support wedges. The easel 1 can also include velcro strips 4 for securing the communication device 2.

The easel 1 is adjustably positioned in three ways to place the communication device in the precise and necessary location for the specific individual using the invention. For example, the easel 1 is adjustably positioned in three ways to place the communication device in the correct location for the specific individual using the invention. For example, the easel 1 is positioned at a height and angle relative to a horizontal plane of a base 5 or a desk top 8 at which the person is seated. The entire easel 1 may be adjustably positioned at a distance from the appendage support 3 through a line perpendicular to a longitudinal line of the human appendage. For example, the easel 1 is positioned away from the appendage support 3 so that a person's arm or elbow is provided support when the person's wrist or hand no longer requires support.

An embodiment of the easel 1 consists of a black acrylic base plate 9, to the top surface of which and at the side edges are bonded ½-inch bronze tinted acrylic parallel side supports 10. The side supports 10 are vertical and perpendicular in relation to the base plate 9. The side supports 10 may have $5/16$ milled side slots 11 parallel to their front edges. These milled slots 11 allow rapid adjustment of the height of the easel table 12. Easel table 12 has a black acrylic communication support edge 13 having a rounded upper surface and velcro strip 4 to secure the communicator to its surface. The easel table 12 may be 4 or more inches higher than the communicator for which it is designed to allow teaching, testing or other material to be clipped to its upper surface. The preferred embodiment of the easel table is matte black or matte dark plastic material. The use of this matte dark material will form a visual ground against which the communication device will visually stand out. This will help keep the person focused on the communication device while using it. The plastic material is also washable, which is a necessary condition for such an apparatus used in a therapeutic setting where many people may use the device each day.

The invention also includes an appendage support 3 for holding a person's appendage, such as a person's hand, wrist, arm, or elbow. The appendage support 3 supports and stabilizes a person's hand, wrist, arm or elbow at a determined height from the base 5.

In another embodiment, the appendage support 3 supports the person's hand, wrist, arm or elbow while providing resistance against the forward or lateral motion of a person's hand, wrist, arm or elbow. The appendage support 3 allows a range of forward, vertical, lateral, and radial movement to enable the person to reach all the keys or pictures on the communication device 2. The appendage support 3 has several design variations to accommodate a wide range of neuromotor disabilities.

In another embodiment, the invention includes a base 5. The base 5 has a top side and a bottom side. The base 5 is preferably made of a flat rigid material such as plastic or wood with non-slip pads bonded to its bottom side that is placed on a table or desk. The base 5 is also preferably made of a washable material with all the sharp corners removed. A base 5 of 16 inches by 22 inches by ¾ inch thick has been found to work well.

The base 5 may have clamp knobs 6 with threaded studs which tighten threaded clamp bars or one long extended bar receiving both studs below the base which serves to secure the entire apparatus to a table or desk 8. The clamp bars may have cork, rubber or other soft padding bonded to its upper surface. The base may have brass bushings inserted in the holes to prevent wear.

The surface of the base 5 is preferably at a height below the subject's eye level such that the person is looking downward toward the communication device as when a person is reading. This desirable line of sight may be achieved with various table and chair heights.

Figure 2:
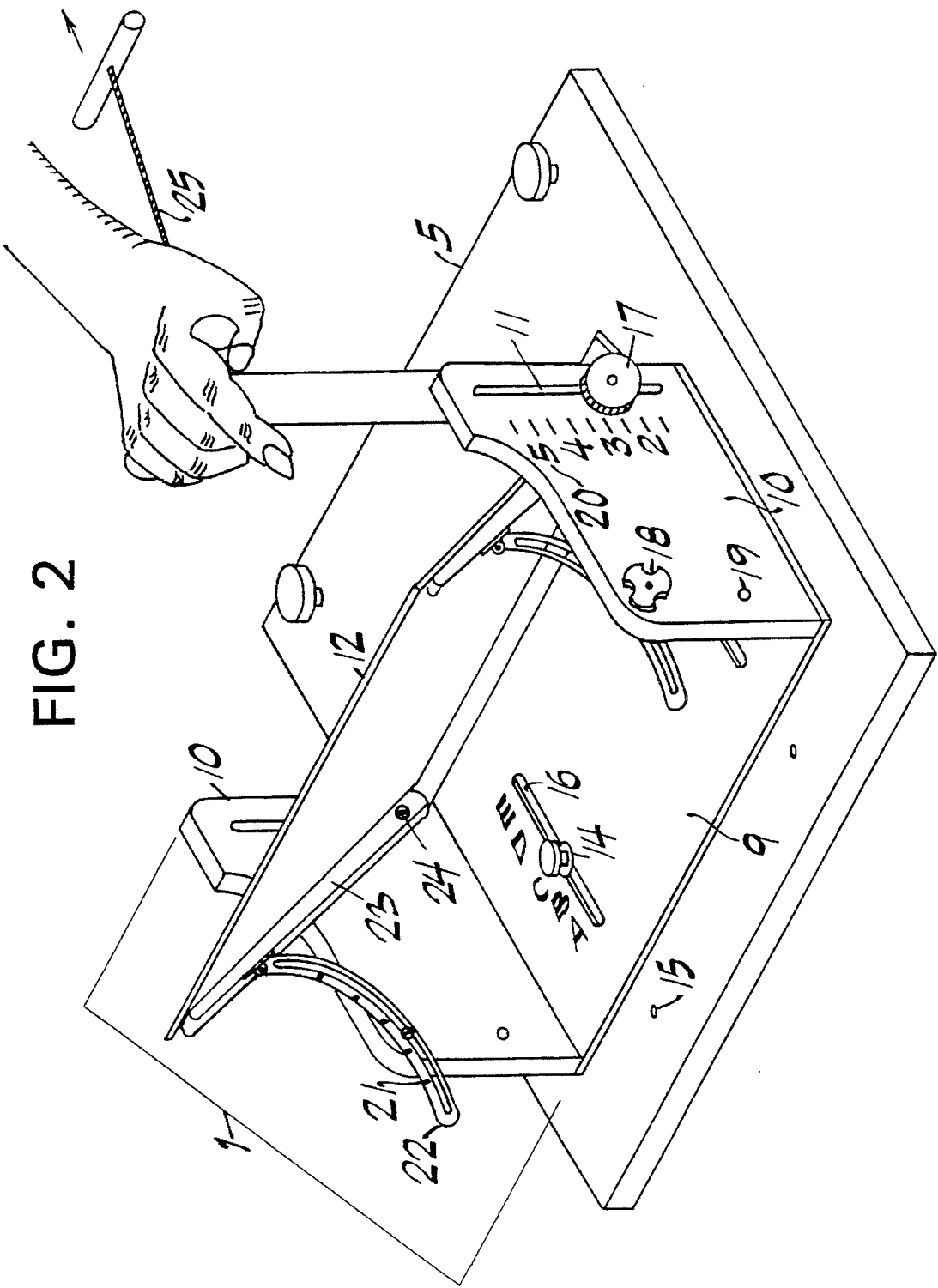
FIG. 2 is a rear perspective view of an embodiment of the invention with a t-bar-type support showing the hand supported as in use.

Referring to FIG. 2, the easel 1 may be attached or mounted to the topside of the base 5 using various attaching means. For example, the easel 1 is attached using bolts and wing screws or knobs with threaded studs 14 that thread into position holes 15 in the base, or velcro tabs. The position of the easel is indexed by noting hole number and letters adjacent to base slot 16 of the easel base plate 9.

The easel 1 may be vertically adjustable, raised or lowered, through a range of 1 inch to 5½ inches in height from the plane of the base 5 by tightening knob 17 at the required position in the side slot 11. The easel 1 may also be adjustable through an arc of 60 degrees relative to the horizontal plane of the base 5 by tightening knob 18 at the correct angle for the disabled person. Knob 18 may be positioned at alternate hole 19 for lower angle settings of the easel. These adjustments enable the communication device to be positioned in the precise and necessary position for a person's individual requirements for pressing the keys. For example, some people need the communication device to be positioned at a high incline due to a limited range of motion. Such height and angle may be indexed by noting the height index numbers 20 on the easel side support 10 and angle reference marks 21 on the slotted bar 22.

The easel 1 may have support wedges 23 which have ¼-inch pivot holes drilled to take the ¼-inch×20 easel pivot screw 24 which is tightened by knob 17. The support wedges give stiffness to the easel table 12 and provide a thick surface to attach the slotted bar 22. The easel may have neoprene or other resilient washers for spacing parts and cushioning all parts that tighten. The neoprene washers may have fender washers placed above them to distribute the pressure evenly to the acrylic plastic. One side of the neoprene washers may have a smooth material such as a plastic film bonded to its surface to prevent the washers from sticking to the easel surface.

FIG. 2 also shows the return prompt tether 25 which is held by the facilitator during certain applications of the invention. The return prompt tether consists of a nylon cord looped around the appendage support mount and extending to a wood handle. The facilitator may give a pull on the cord to increase forward resistance or may give a tug to the cord to prompt the student to pull the hand back from the keyboard when needed (arrow shows direction of pull).

Several types of appendage supports 3 can be used in the system of the present invention. Examples of appendage supports 3 are: a t-bar-type support, hand-cradle-type support, arm-rest-type support, elbow-cradle-type support, and a pointer-grip-type support.

Referring to FIG. 3, the hand-cradle-type support 3A holds a person's hand and envelopes the fingers. The hand-cradle-type support 3A can be custom made to fit a particular person. For example, the hand-cradle-type support 3A may be tapered to allow a snug fit. The hand-cradle-type support 3A may also be lined with foam rubber 26 to cushion and grip a person's hand. The hand-cradle-type support 3A may also be covered with leather, vinyl, or cloth to protect the foam rubber from eroding or being picked away. The hand-cradle-type support 3A can be made of high-strength rigid heat-molded plastic or forged of aluminum 27. In an alternative embodiment, the hand-cradle-type support 3A can hold a person's wrist and envelope the hand.

In an embodiment of the appendage support 3A, the bottom of the appendage support 3A or the side of the appendage support 3A facing downward is drilled and countersunk for two 6×32 machine screws to attach the appendage support 3A to a support mount 28 consisting of a ¼-inch brass pipe formed to a ⅛×¾×2½ inch steel plate which can be drilled and tapped to take the 6×32 screws. Access to the screw heads can be made possible by holes 29 in the leather and foam liner on the side of the appendage support 3A facing upward. A cloth or elastic strap 30 can be attached to the appendage support 3A for securing a person's hand in the appendage support 3A. The strap is placed around the back of the hand and may be secured by a velcro tab 31 or buckle.

Referring to FIG. 3, an arm rest-type support 3B may also be used. An arm rest-type support 3B is preferably made from molded plastic or forged aluminum half sleeve, lined with foam rubber covered with cloth or vinyl. In addition, the arm rest-type support 3B may have cloth or elastic straps with velcro tab to secure the arm to the arm rest-type support 3B. The velcro straps ensure the arm does not slide forward and back in the arm rest.

Referring to FIG. 3, an elbow-cradle-type support 3C holds a person's elbow. The elbow-cradle-type support 3C is preferably made of forged and riveted aluminum, lined with foam rubber, and covered in cloth. The elbow-cradle-type support 3C holds the arm and forearm with elastic or webbing straps fastened with velcro.

Referring to FIG. 4D, a t-bar-type support 4D is held by a person's hand while the person points an index finger to type on the keyboard (as illustrated in FIG. 2). The t-bar-type support may be made of a solid high-strength plastic or wood cylinder 32 with a steel bar bonded within 33. It may have molded foam 34 and be covered with cloth, leather, vinyl or sheepskin. The t-bar-type support enables a person to steady or stabilize their hand while using the communication device. The t-bar-type support is especially suitable for people who are able to point an index finger.

Referring to FIG. 4E, a pointer-grip-type support 4E is suitable for people with motor impairment who cannot point an index finger. This type of support includes a ball 35 or other interchangeable shaped grip which is somewhat soft and may be squeezed when in use. The pointer is made of a ¼-inch brass rod 36 which is threaded on one end and screwed into a threaded hole in a tilt plate 37. The rod 36 has a brass tube 38 which slides over the rod 36. The end of the tube 38 has a rubber or other soft tip 39 and within the tube 38 and along its axis is a compression spring 40. When the pointer tip 39 is pressed against the keyboard the pointer tip 39 and tube 38 slide down the rod 36 against the spring 40. This prevents excess force from being applied to the keys by the person's poor motor control. The ball 35 is bonded to a brass cup with a ¼-inch×20 nut brazed onto its lower surface 41. The threaded nut allows the ball grip to be interchangeable as needed for persons of different hand size. The tilt plate 37 has a ¼-inch×20 flathead screw 42 braised to its upper surface. The tilt plate 37 has a ¼-inch pivot hole with a ¼-inch recessed pivot pin 43 about which the pointer assembly (parts 35 through 42) tilts through an arc 30 degrees indicated by arrows. The pointer grip mount 44 is a ¼-inch brass pipe which has a ⅜-inch milled slot at its upper end. The pipe 44 has a ¼-inch hole drilled to take the pivot pin 43. The pivot pin 43 is threaded at one end and screws into the pipe 44 to secure its position. The tilt plate 37 has a ¹⁄₁₆-inch hole drilled at its lower surface to receive the upper end of the tension spring 45. The tension spring 45 is supported by a No. 10 screw 46 which is screwed into a threaded hole in the pointer grip mount 44. The tension spring 45 offers resistance to upward and downward movement of the pointer assembly. The tension spring 45 is kept in alignment by a wood plug 47. The pointer-grip-type support can also include a strap or elastic band with velcro tabs or buckle to hold the person's hand in position.

Referring to FIG. 4F, the pointer-grip-type support is shown in perspective view with the facilitator control handle 48 attached. For certain people, the facilitator or therapist may want to be able to guide the person's hand or arm while the hand or arm is being held by or is holding an appendage support. The facilitator control handle 48 screws into a ¼-inch×20 rod coupling brazed to a ¼-inch by 20 nut 49 which is threaded onto the screw of the mount.

Referring to FIG. 5, the appendage support 3 can be attached to the forward resistance spring assembly 50 and the support mount 51. A forward resistance spring assembly 50 includes a ¼-inch steel support pipe 52 threaded into a ¼-inch pipe coupling with a ¼-inch pipe nipple threaded and soldered to its lower end 53. This coupling 53 serves to make the height of the outer support spring 54 adjustable in height. The spring 54 is mounted 1½ inches lower when the coupling 53 is removed from the apparatus as needed. The support pipe 52 or the coupling 53 are threaded into a ¼×½-inch steel pipe bushing 55 which is held to a base 5 with a steel hex nut 56 threaded onto its lower end. The hex nut 56 is recessed in a hole counterbored in the bottom of the base 5.

Fitted over the support pipe 52 is a 6-inch long heavy extension spring 54 into which is fitted at the upper end the support mount 51 or support mount 28 (shown in FIG. 3). The various appendage supports are attached to the mount 51 or 28 and are held at a determined plane above a horizontal plane of base 5. The support mount 51 can be a ¼-inch brass pipe 57 to which can be threaded a hexagon brass cap nut 58 with a ¼-inch×20 brass flathead machine screw 59 brazed to its end surface. Alternatively, the support mount 28 (as shown in FIG. 3) can be a ¼-inch brass pipe to which can be brazed a ⅛×¾×2½-inch steel plate. Different types of mounts are needed to support the various types of appendage supports required by the various types of disabilities.

As various degrees of force are needed to offer resistance to the forward motion of the person's hand, a selection of outer support springs of different wire diameter can be available as needed by the facilitator therapist. As a means of further increasing the resistance of the outer support spring 54, an inner tension spring 60 may be fitted over a brass pin 61 which is threaded into a support pipe 52. The inner tension spring 60 has a plastic sleeve 62 placed over it to reduce noise. The outer spring 54 may be oiled lightly and covered during assembly with a heavy foam sleeve 63 to reduce noise and offer protection so the outer spring does not pinch the person when in use. The two springs 54 and 60, one inside the other, can provide a resistance of 2 to 8 pounds of force against forward movement of a person's hand typing a communication. The forward resistance spring assembly 50 is assembled during manufacture to give a specific resistance as needed by the individual using the device or may be set up by the facilitator therapist prior to use by a client. A selection of springs is available for the invention as may be needed by a speech therapist.

Also referring to FIG. 5, the base 5 may have two parallel series of threaded holes 15 parallel to opposite edges of the base 5 to secure an easel to the base 5 in the desired position by use of screws or threaded studs or bolts. The threaded holes 15 may be referenced so that an easel can be quickly adjusted to a person's setting, especially where several people may use the same apparatus.

Also referring to FIG. 5, the base 5 may have two knobs 6 with threaded studs which pass through washer 64 and thread into t-nut 65 which are set into the bottom of clamp bar 7 which secures the entire apparatus firmly to the table top. The clamp bars 7 have rubber or cork pads 66 bonded to their upper surface.

The foam sleeve 63 may be covered with cloth or vinyl. The foam sleeve is capped by 1½-inch black fender washer 67 held in place by a ¼-inch×20 hex nut 68.

I claim:

1. A communication facilitation system comprising:
   a. an easel for supporting a communication device;
   b. a human appendage support operatively associated with the easel; and
   c. a base having a top side and a bottom side, wherein the easel is mounted to the top side of the base and wherein the base has two knobs with threaded studs which thread into clamp bars below the base, which hold the entire apparatus firmly to the tabletop.

2. The apparatus of claim 1 wherein the human appendage support is a t-bar-type support.

3. The apparatus of claim 1 wherein the human appendage support is a hand cradle-type support.

4. The apparatus of claim 1 wherein the human appendage support is a pointer-grip-type support.

5. The apparatus of claim 1 wherein the human appendage support is an arm-rest type support.

6. The apparatus of claim 1 wherein the human appendage support is an elbow-cradle-type support.

7. A communication facilitation system comprising:
   a. an easel for supporting a communication device;
   b. tensioned human appendage support operatively associated with the easel;
   c. a base having a top side and a bottom side; wherein the easel is mounted to the top side of the base and wherein the base has two parallel series of threaded holes, parallel to opposite edges of the base; and
   d. means for securing the easel to the base through the threaded holes.

8. A communication facilitation system comprising:
   a. an easel for supporting a communication device;
   b. a human appendage supporting operatively associated with the easel;
   c. a forward resistance spring assembly and a support mount operatively associated with the human appendage support;
   d. a base having a top side and bottom side; wherein the easel is mounted to the top side of the base and wherein the base has two parallel series of threaded holes, parallel to opposite edges of the base; and
   e. means for securing the easel to the base through the threaded holes.

9. The apparatus of claim 8 wherein the forward resistance spring assembly provides a resistance against movement of the appendage support toward the easel from 2 to 8 pounds of force.

10. The apparatus of claim 8 further comprising a facilitator control handle.

11. A communication facilitation system comprising:
   a. an easel for supporting a communication device;
   b. a human appendage support operatively associated with the easel;
   c. a forward resistance spring assembly and a support mount operatively associated with the human appendage support; and
   d. a return prompt tether for providing added resistance against movement of the appendage support.

* * * * *